(12) United States Patent
Collins

(10) Patent No.: US 11,471,271 B2
(45) Date of Patent: *Oct. 18, 2022

(54) INTRAOCULAR LENS HAVING AN ASYMMETRIC HINGED CLOSED-LOOP HAPTIC STRUCTURE

(71) Applicant: Alcon Inc., Fribourg (CH)

(72) Inventor: Stephen John Collins, Fort Worth, TX (US)

(73) Assignee: Alcon Inc., Fribourg (CH)

(*) Notice: Subject to any disclaimer, the term of this patent is extended or adjusted under 35 U.S.C. 154(b) by 0 days.

This patent is subject to a terminal disclaimer.

(21) Appl. No.: 17/140,740

(22) Filed: Jan. 4, 2021

(65) Prior Publication Data
US 2021/0121285 A1    Apr. 29, 2021

Related U.S. Application Data

(63) Continuation of application No. 16/059,735, filed on Aug. 9, 2018, now Pat. No. 10,912,642.

(60) Provisional application No. 62/547,140, filed on Aug. 18, 2017.

(51) Int. Cl.
*A61F 2/16* (2006.01)

(52) U.S. Cl.
CPC .............. *A61F 2/1613* (2013.01); *A61F 2/16* (2013.01); *A61F 2/1662* (2013.01); *A61F 2002/1681* (2013.01); *A61F 2002/1683* (2013.01); *A61F 2002/1686* (2013.01); *A61F 2002/16901* (2015.04)

(58) Field of Classification Search
CPC ............ A61F 2/1694; A61F 2002/1681; A61F 2002/1683; A61F 2002/1686; A61F 2002/16901; A61F 2002/169053; A61F 2/1648

See application file for complete search history.

(56) References Cited

U.S. PATENT DOCUMENTS

| 4,249,271 | A | * | 2/1981 | Poler | A61F 2/16 623/6.41 |
| 4,990,159 | A | * | 2/1991 | Kraff | A61F 2/1613 623/6.49 |
| 7,150,760 | B2 | * | 12/2006 | Zhang | A61F 2/1629 623/6.37 |
| 2006/0161252 | A1 | * | 7/2006 | Brady | A61F 2/1629 623/6.37 |
| 2010/0286772 | A1 | * | 11/2010 | Privat de Fortune | A61F 2/1613 623/6.37 |

(Continued)

*Primary Examiner* — Javier G Blanco
(74) *Attorney, Agent, or Firm* — Patterson + Sheridan, LLP

(57) ABSTRACT

An ophthalmic device includes an optic having an optic axis and a closed-loop haptic structure coupled with the optic. The closed loop haptic structure includes a first hinge having a first section, a second section, and a connecting section extending between the first section and the second section. The first section has a first component extending in a first angular direction and a second component extending in a second angular direction that is opposite to the first angular direction. The closed loop haptic structure further includes a second hinge including a radial section and an axial section extending from the axial section in the first angular direction, the radial section having a cross-sectional area greater than a maximum cross-sectional area of the first hinge.

4 Claims, 3 Drawing Sheets

(56) References Cited

U.S. PATENT DOCUMENTS

2011/0282441 A1\* 11/2011 Zadno-Azizi ......... A61F 2/1648
623/6.37

\* cited by examiner ical lenses (IOLs). The following description
INTRAOCULAR LENS HAVING AN ASYMMETRIC HINGED CLOSED-LOOP HAPTIC STRUCTURE

PRIORITY CLAIM

This application is a continuation of U.S. Non-Provisional patent application Ser. No. 16/059,735, filed on Aug. 9, 2018 and claims the benefit of priority of U.S. Provisional Patent Application Ser. No. 62/547,140 titled "INTRAOCULAR LENS HAVING AN ASYMMETRIC HINGED CLOSED-LOOP HAPTIC STRUCTURE," filed on Aug. 18, 2017, whose inventor is Stephen John Collins, which is hereby incorporated by reference in its entirety as though fully and completely set forth herein.

FIELD

The present disclosure relates generally ophthalmic lenses and, more particularly, to intraocular lenses having asymmetric hinged closed-loop haptic structures.

BACKGROUND

Intraocular lenses (IOLs) may be implanted in patients' eyes to replace a patient's natural lens. An IOL typically includes (1) an optic that corrects the patient's vision (e.g., typically via refraction or diffraction), and (2) haptics that constitute support structures that hold the optic in place within the patient's eye (e.g., within capsular bag). In general, a physician selects an IOL for which the optic has the appropriate corrective characteristics for the patient. During ophthalmic surgery, often performed for conditions such as cataracts, the surgeon implants selected IOL by making an incision in the capsular bag of the patient's eye (a capsulorhexis) and inserting the IOL through the incision. Typically, the IOL is folded for insertion into the capsular bag via a corneal incision and unfolded once in place within the capsular bag. During unfolding, the haptics may expand such that a small section of each bears on the capsular bag, retaining the IOL in place.

Although existing IOLs may function acceptably well in many patients, they also have certain shortcomings. For example, existing IOL design may include haptics that cause striae, or folds, in the posterior capsular bag. Such striae may result from the haptics having a relatively small angle of contact with the capsular bag. Because striae may negatively impact patient outcomes (e.g., by resulting in increased posterior capsular opacification (PCO) by providing a mechanism for the growth and/or migration of cells), haptic designs that reduce striae are desirable. Moreover, such designs should also have a volume and foldability conducive to maintaining acceptably small incision sizes (e.g., 3 mm or less) as larger incision may adversely affect the patient's recovery.

Accordingly, what is needed is an improved IOL that may address PCO without significantly complicating implantation.

BRIEF SUMMARY OF THE INVENTION

An ophthalmic device includes an optic having an optic axis and a closed-loop haptic structure coupled with the optic. The closed loop haptic structure includes a first hinge having a first section, a second section, and a connecting section extending between the first section and the second section. The first section has a first component extending in a first angular direction and a second component extending in a second angular direction that is opposite to the first angular direction. The closed loop haptic structure further includes a second hinge including a radial section and an axial section extending from the axial section in the first angular direction, the radial section having a cross-sectional area greater than a maximum cross-sectional area of the first hinge.

According to the method and system disclosed herein, the closed-loop haptic structure may result in fewer striae and reduced PCO. Consequently, performance of the ophthalmic device may be improved.

BRIEF DESCRIPTION OF SEVERAL VIEWS OF THE DRAWINGS

For a more complete understanding of the present disclosure and the advantages thereof, reference is now made to the following description taken in conjunction with the accompanying drawings in which like reference numerals indicate like features and wherein.

The skilled person in the art will understand that the drawings, described below, are for illustration purposes only. The drawings are not intended to limit the scope of the applicant's disclosure in any way.

DETAILED DESCRIPTION OF THE PREFERRED EMBODIMENTS

The exemplary embodiments relate to ophthalmic devices such as intraocular lenses (IOLs). The following description is presented to enable one of ordinary skill in the art to make and use the invention and is provided in the context of a patent application and its requirements. Various modifications to the exemplary embodiments and the generic principles and features described herein will be readily apparent. Phrases such as "exemplary embodiment", "one embodiment" and "another embodiment" may refer to the same or different embodiments as well as to multiple embodiments. The embodiments will be described with respect to systems and/or devices having certain components. However, the systems and/or devices may include more or less components than those shown, and variations in the arrangement and type of the components may be made without departing from the scope of the invention. Thus, the present invention is not intended to be limited to the embodiments shown, but is to be accorded the widest scope consistent with the principles and features described herein.

In general, the present disclosure relates to an ophthalmic device having an optic including an optic axis and a closed-loop haptic structure coupled with the optic. The closed loop haptic structure includes a first hinge having a first section, a second section, and a connecting section extending between the first section and the second section. The first section has a first component extending in a first angular direction and a second component extending in a second angular direction that is opposite to the first angular direction. The closed loop haptic structure further includes a second hinge including a radial section and an axial section extending from the axial section in the first angular direction, the radial section having a cross-sectional area greater than a maximum cross-sectional area of the first hinge.

Figure 1A:
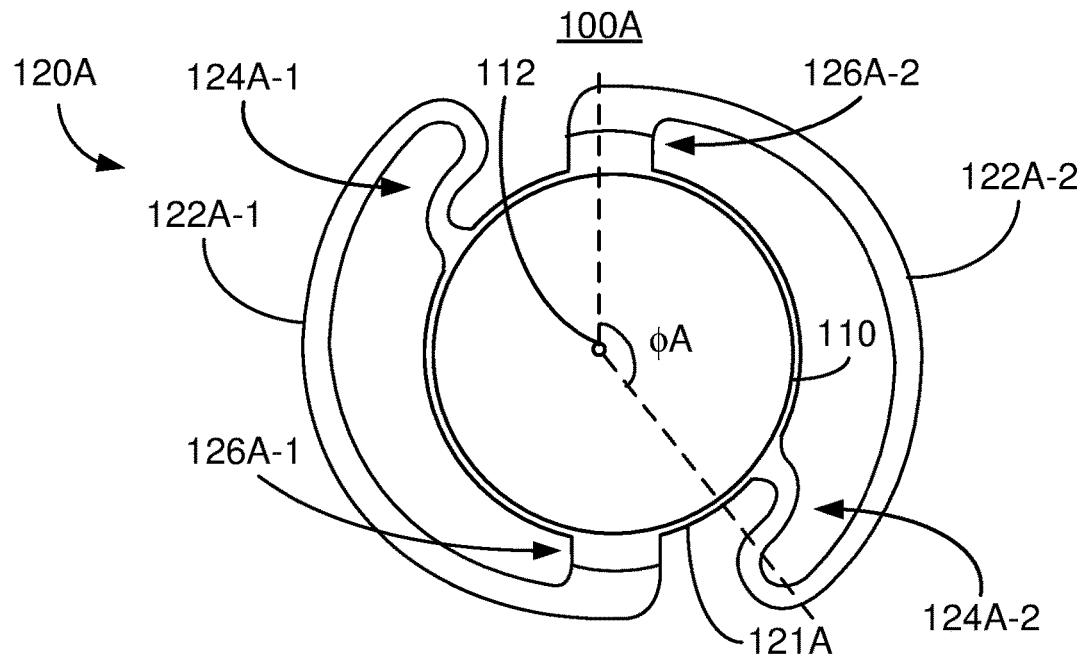
FIGS. 1A-1E depict various views of an exemplary embodiment of an ophthalmic device having an asymmetric hinged closed-loop haptic structure.
Figure 1B:
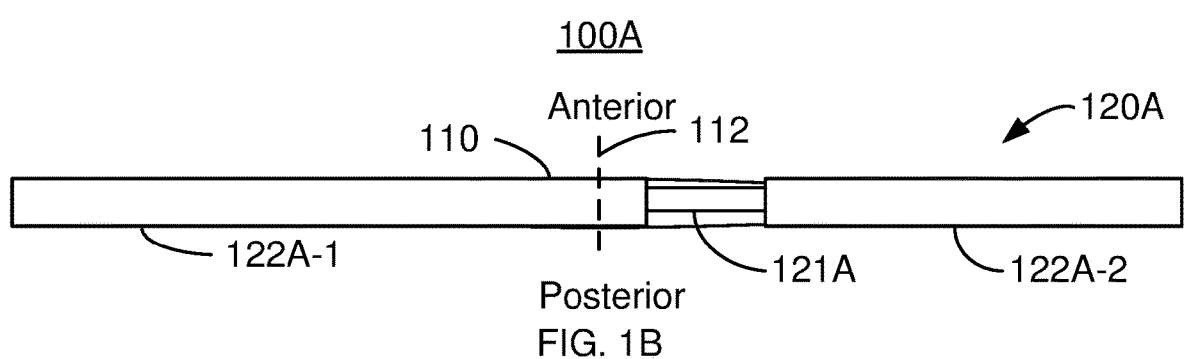
Figure 1C:
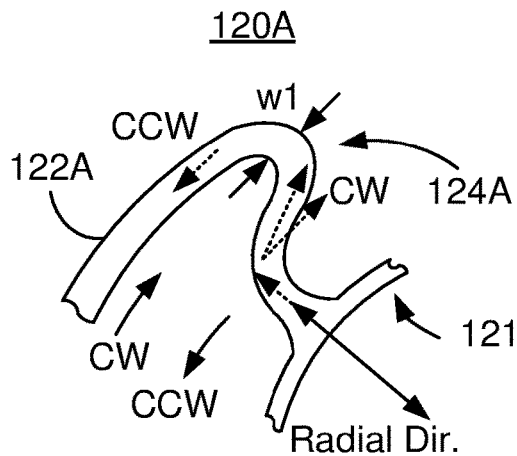
Figure 1D:
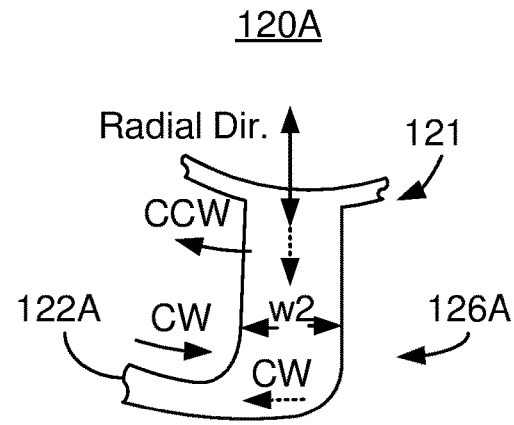
Figure 1E:
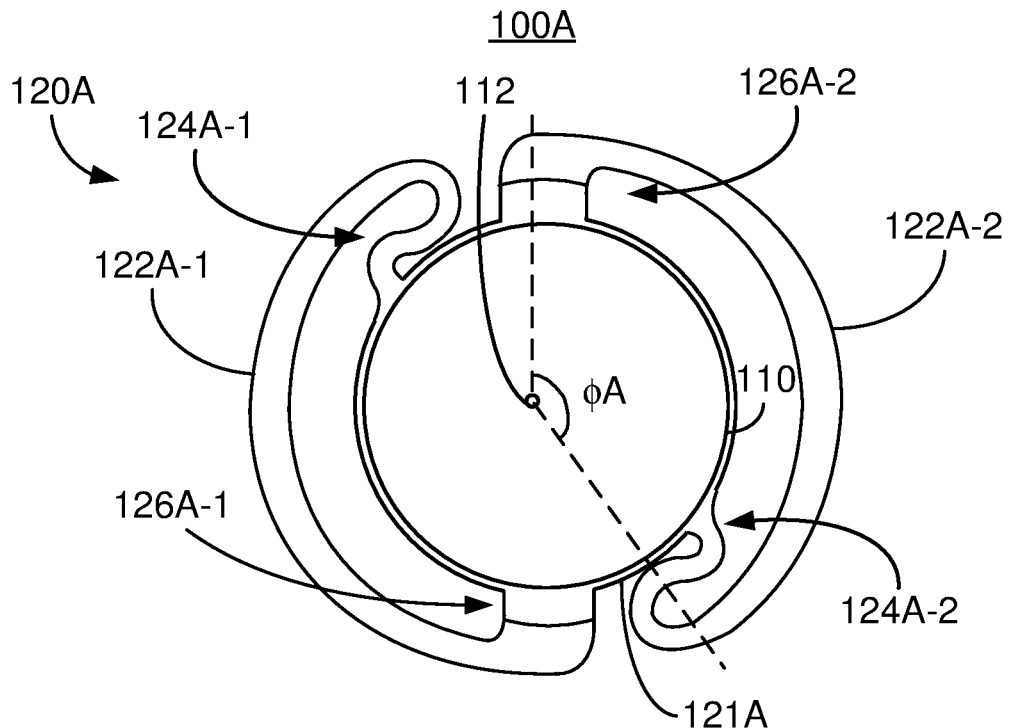

FIGS. 1A-1E depict various views of an exemplary embodiment of an ophthalmic device 100A having an optic 110 and a closed-loop haptic structure 120A. For simplicity, the ophthalmic device 100A is also referred to as an IOL 100A. FIG. 1A depicts a plan view of the IOL 100A, while FIG. 1B depicts a side view of the IOL 100A. FIGS. 1C and D depict plan views of portions of the IOL 100A. FIG. 1E depicts a plan view of the IOL 100A under the influence of a compressive force. For clarity, FIGS. 1A-1E are not to scale and not all components may be shown.

The optic 110 is an ophthalmic lens 110 that may be used to correct a patient's vision. For example, the optic may be a refractive and/or diffractive lens. The optic 110 may be a monofocal lens, multifocal lens, a toric lens and/or another type of lens. The anterior and/or posterior surface of the optic 110 may thus have features including but not limited to a base curvature and diffraction grating(s). The optic 110 may refract and/or diffract light to correct the patient's vision. The optic 110 has an optic axis 112 that is out of the plane of the page in FIG. 1A. The optic 110 is depicted as having a circular footprint in the plan view of FIG. 1A. In other embodiments, the optic 110 may have a differently shaped footprint. In some embodiments, the optic 110 may also include other features that are not shown for clarity. The optic 110 may be formed of one or more of a variety of flexible optical materials. For example, the optic 110 may include but is not limited to one or more of silicone, a hydrogel and an acrylic such as AcrySof®.

The closed-loop haptic structure 120A is a support structure used to hold the ophthalmic device 100A in place in the capsular bag of a patient's eye (not explicitly shown). In some embodiments, the closed-loop haptic structure 120A is formed of the same material as the optic 110. The closed-loop haptic structure 120A includes an optional frame 121 and closed loops 122A-1 and 122A-2 (collectively or generically termed closed loops 122A). The loops 122A include hinges 124A-1, 124A-2, 126A-1 and 126A-2. The hinges 124A-1 and 124A-2 (collectively or generically 124A) have similar form and function. Similarly, hinges 126A-1 and 126A-1 (collectively or generically 126A) are analogous in structure and function.

The frame 121 couples the closed-loop haptic structure haptic 120A with the optic 110. The inner portion of the frame 121 may be desired to match the shape of the optic 110. Thus, the inner edge of the frame 121 shown as circular in FIG. 1A may have a different shape. The outer edge of the frame 121 can but need not match the inner edge. In some embodiments, the closed-loop haptic structure 120A and the optic 110 may be molded together. Thus, the optic 120A and haptic may form a single monolithic structure. In other embodiments, the frame 121 may be otherwise attached to the optic 110. For example, the frame 121 may be bonded to or molded around a preexisting optic 110. In some such embodiments, some or all of the haptic structure 120A may be formed of a different material than the optic 110. In some embodiments, the frame 121 is omitted. In such embodiments, closed loops 122A may be coupled directly to the optic 110. The optic 110 and closed loops 122A may be separated bonded or formed together in these embodiments.

The closed loops 122A-1 and 122A-2 retain the IOL 100A in position in the patient's eye by bearing on the capsular bag. Each loop 122A subtends an angle, ϕA. The outer edge of the loops 122A subtending the angle ϕA bear on the capsular bag. This angle ϕA may be greater than ninety degrees. For example, the angle ϕA may be at least one hundred and twenty degrees. In some embodiments, the angle ϕA may be at least one hundred and thirty-five degrees. However, the angle ϕA is generally less than one hundred and eighty degrees. Together the loops 122A-1 and 122A-2 may subtend an angle of 2ϕ, which is greater than one hundred and eighty degrees. In some embodiments, the loops 122A may together subtend an angle of at least two hundred and forty degrees. Consequently, the loops 122A contact the capsular bag over a large angle. The capsular bag may thus be extended over a larger volume.

Although two loops 122A are shown in FIG. 1A, more loops may be used in other embodiments. For example, three or four loops analogous to the loops 122A may be present. In such a case, each loop subtends a smaller angle. However, the total of the angles subtended by all the loops remains large. The loops 122A shown are substantially the same and subtending the same angle. In other embodiments, different loops may subtend different angles. However, the combination of loops still subtend a large angle. The loops 122A may thus stretch the capsular bag over a significantly larger region than for haptics having open arms. This may reduce striae and, therefore, PCO.

Each of the closed loops 122A includes two hinges 124A and 126A. Although two of each hinge 124A and 126A (one of each hinge for each loop 122A) are shown, another number could be present in another embodiment. Further, the pair of hinges 124A and 126A need not be present for every loop of the haptic structure.

The hinges 124A are configured such that a portion of the closed loop 122A extends radially beyond the attachment point to the frame 121. In the embodiment shown in FIGS. 1A and 1C, the closed loops 122A extend past the attachment point. Thus, a hinge 124A may have a first section having a component that extends in one angular direction, a second section having a component that extends in the opposite angular direction, and a connecting section between the first and second sections. The connecting section has a bend that may be close to one hundred and eighty degrees. This bend is the portion of the loop 122A that extends furthest past the attachment point. This may be seen in the embodiment of the hinge 124A depicted in FIG. 1C. The hinge 124A is connected to the frame 121 at or near the radial direction. However, in other embodiments, the hinge 124A may have a small component in the clockwise (CW) direction or in the counter clockwise (CCW) direction. The connection the hinge 124A/loop 122A makes with the frame 121 may be within sixty degrees of the radial direction. In some embodiments, the connection the hinge 124A/loop 122A makes with the frame is within forty-five degrees of the radial direction. In some embodiments, this angle is within twenty degrees of the radial direction.

As illustrated by FIG. 1C, hinge 124A may have a first section that has component in the CW direction. The direction of the first section and the CW component are shown by dotted arrows. As depicted in FIG. 1C, the first section of the hinge 124A may have a relatively large component in the CW direction. In some embodiments, the first section of the hinge 124A is within forty-five degrees of the CW direction. The first section of the hinge 124A may be within twenty degrees of the CW in some such embodiments. The second section of the hinge 124A is substantially in the CCW direction, as shown by the dotted arrow at the outer edge of the loop 122A. In some embodiments, the second section of the hinge 124A is within twenty degrees of the CCW direction. Between the first and second sections is a connecting section that includes a bend. This bend may be close to one hundred and eighty degrees and is sufficient such that the loop 122A changes direction from generally CW to CCW. In other embodiments or locations, the angular directions may be reversed. For example, if the locations of the hinges 124A and 126A were reversed, the first section of hinge 124A would be in the CCW direction and the second section would be in the CCW direction. In the embodiment shown, the hinge 124A has a relatively constant width w1 and a relatively constant thickness in a direction perpendicular to the page. In other embodiments, different portions of the hinge 124A may have different widths and/or different thicknesses.

As illustrated by FIG. 1D, hinge 126A may be configured with two sections. A first section is substantially radial. This radial section connects to the frame 121 or the optic 110 if the frame 121 is omitted. An axial section of the hinge is in the opposite angular direction as the second section of the hinge 124A. This is because the second section of the hinge 124A and the axial section of the hinge 126A are connected to form the outer edge of the loop 122A. The radial section extends outwardly from the frame 121. The axial section is in the CW direction and connected to the radial section through a bend that is substantially ninety degrees. The radial section of the hinge 126A has a width w2 and a thickness in a direction perpendicular to the page.

The hinges 124A and 126A are asymmetric. In certain embodiments, the hinges 124A may be more readily bent than the hinges 126A. In the embodiment shown, this is because the cross-sectional area of the axial radial section of the hinge 126A is larger than the cross-sectional area of the hinge 124A. In the embodiment shown in FIGS. 1A-1E, the thickness of the loop 122A is constant. Because the width w2 of a portion of the hinge 126A is greater than the width w1 of the hinge 124A, the hinge 126A is more stable. In some embodiments, w2 is at least twice w1. IN other embodiments, w2 is at least thrice w1. In other embodiments, the thickness of the hinge 126A may be greater than the thickness of the hinge 124A and the widths may be the same. In other embodiments, the widths and thicknesses may vary in another manner such that the hinge 126A is more stable than the hinge 124A. Alternatively, the hinge 126A may include other, stiffer materials than the hinge 124A. All of the above may be considered ways in which the cross-sectional area of the hinge 124A and is less than the cross-sectional area of the hinge 126A such that the hinge 126A is stiffer than the hinge 124A.

Because the hinges 124A and 126A are asymmetric, the loops 122A are more likely to stay in-plane when compressed. The hinges 124A and hinges 126A are configured such that the closed-loop haptic structure 120A may be compressed without significant motion in the anterior or posterior direction. FIG. 1E depicts the closed-loop haptic structure 120A under a compressive force. Because of the hinges 124A-1, 124A-2, 126A-1 and 126A-2, the compression has caused the connecting section of each hinge 124A to bend further. The hinges 126A have remained relatively stable. The first and second sections of the hinges 124A are brought closer together. As a result, a portion of the loops 122A-1 and 122A-2 extend further past the connection of the hinge 124A to the frame 121 than in the uncompressed state shown in FIG. 1A. The outer edges of the loops 122A also move closer to the optic axis 112. However, the haptic structure 120A has remained substantially in-plane. The optic 110 has also remained substantially in-plane. Although it is possible for the optic 110 to move in the anterior or posterior direction (i.e. along the optic axis 112) due to the compressive force, this tendency may be mitigated by the combination of the hinges 124A and 126A. Thus, motion of the optic 110 and haptic structure 120A may be more predictable.

As can also be seen in FIG. 1B, the closed loop haptic structure 120A includes sharp corners. Both the loops 122A and the frame 121 may have sharp edges. As a result, the optic 110 may be surrounded on all sides by sharp edges. These sharp edges may also reduce the probability of cells migrating to the optic 110 from any side. Again, PCO may be reduced or eliminated.

Use of the IOL 100A may improve patient outcomes. The large angle $\phi A$ allows the closed-loop haptic structure to contact a larger portion of and better extend the capsular bag. This may not only improve the axial and rotational stability of the IOL 100A, but also reduce the formation of striae (wrinkles) in the capsular bag. The large angle of contact with the capsular bag may thus mitigate or prevent PCO. Sharp edges for the closed-loop haptic structure 120A may further reduce PCO. Hinges 124A-1, 124A-2, 126A-1 and 126A-2 allow the closed-loop haptic structure 120A to respond more predictably to compression. More specifically, the loops 122A-1 and 122A-2 and optic 110 are more likely to remain in plane in response to a compression. Damage to the patient's iris may be prevented. Thus, performance of the IOL 100A may be further improved.

Figure 2:
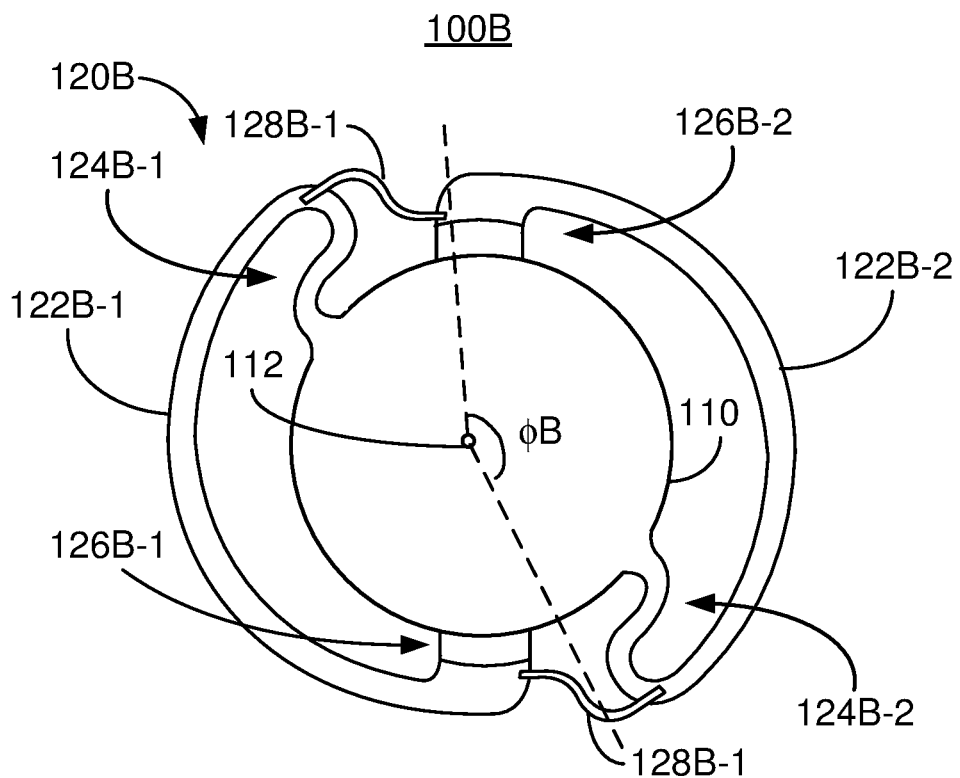
FIG. 2 depicts another exemplary embodiment of an ophthalmic device having an asymmetric hinged closed-loop haptic structure.

FIG. 2 depicts another exemplary embodiment of an ophthalmic device 100B having an optic 110 and a closed-loop haptic structure 120B. For simplicity, the ophthalmic device 100B is also referred to as an IOL 100B. The IOL 100B is analogous to the IOL 100A. Consequently, analogous components have similar labels. Thus, the optic 110 and closed-loop haptic structure 120B are analogous to the optic 110 and closed-loop haptic structure 120A. For clarity, FIG. 2 is not to scale and not all components may be shown.

The optic 110 may be a refractive and/or diffractive lens and may be monofocal or multifocal. The closed-loop haptic structure 120B includes closed loops 122B-1 and 122B-2 (collectively or generically 122B) hinges 124B-1 and 124B-2 (collectively or generically 124B) and hinges 126B-1 and 126B-2 (collectively or generically 126B) that are analogous to closed loops 122A-1 and 122A-2, hinges 124A-1 and 124A-2, and hinges 126A-1 and 126A-2, respectively. In the embodiment shown in FIG. 2, the frame is omitted. Thus, the loops 122B are connected to the optic 110. However, in other embodiments, the frame might be included. The haptic structure 120B and optic 110 may be fabricated together or formed separately and then connected.

The closed loops 122B retain the IOL 100B in position in the patient's eye by bearing upon the capsular bag. Each of the loops 122B subtends an angle, $\phi B$. In some embodiments, the magnitude of $\phi B$ is substantially the same as that for $\phi A$. In other embodiments, $\phi B$ may be larger than $\phi A$. For example, $\phi B$ may be as large as one hundred and eighty degrees.

The hinges 124B and 126B are configured and function in an analogous manner to the hinges 124A and 126A, respectively. Each hinge 124B thus includes a first section having a component in a first angular direction (e.g. CW or CCW), a second section having a component in a second angular direction (e.g. CCW or CW, respectively) and a connecting section between the first and second sections. As a result, one or more of the loops 122B has a portion that extends past the attachment point to the optic 110 for the hinge 124B. Similarly, each hinge 126B has a radial section and an axial section that are connected through a bend that is substantially ninety degrees. The axial section is in the angular direction that is opposite to the second section of the first hinge because these two sections meet in the loop 122B. Each hinge 126B is stiffer in at least the radial section than the hinge 124B. For example, at least the radial section of the hinge 126B has a larger cross-sectional area, has a larger thickness, has a larger width and/or is formed of a stiffer material than the relevant portions of the hinge 124B. As a result, the hinge 126B is more stable than the hinges 122. Although each of the closed loops 122B is shown as including two hinges, in another embodiment, each loop 122B may have another number of hinges 124B and/or 126B. Further, although two loops 122B are shown, in another embodiment, another number of loops might be present.

In addition, the haptic structure 120B includes connectors 128B-1 and 128B-2 (collectively or generically 128B). The connector 128B-1 connects the hinge 124B-1 to the hinge 126B-2. The connector 128B-3 and 128B-2 connect the hinge 124B-1 to the hinge 126B-2. These connectors 128B may improve the stability of the haptic structure 120B and help ensure that the loops 122B remain in plane when under compression.

The IOL 100B may share some or all of the benefits of the IOL 100A. The large angle ϕB allows the closed-loop haptic structure 120B to contact a larger portion of the capsular bag. This may improve the stability of the IOL 100B, reduce striae in the capsular bag, and mitigate or prevent PCO. Sharp edges for the closed-loop haptic structure 120B may further reduce PCO. Hinges 124B and 126B allow the closed-loop haptic structure 120B to respond more predictably to and be more likely to remain in plane in response to a compression. Thus, performance of the IOL 100B may be improved.

Figure 3:
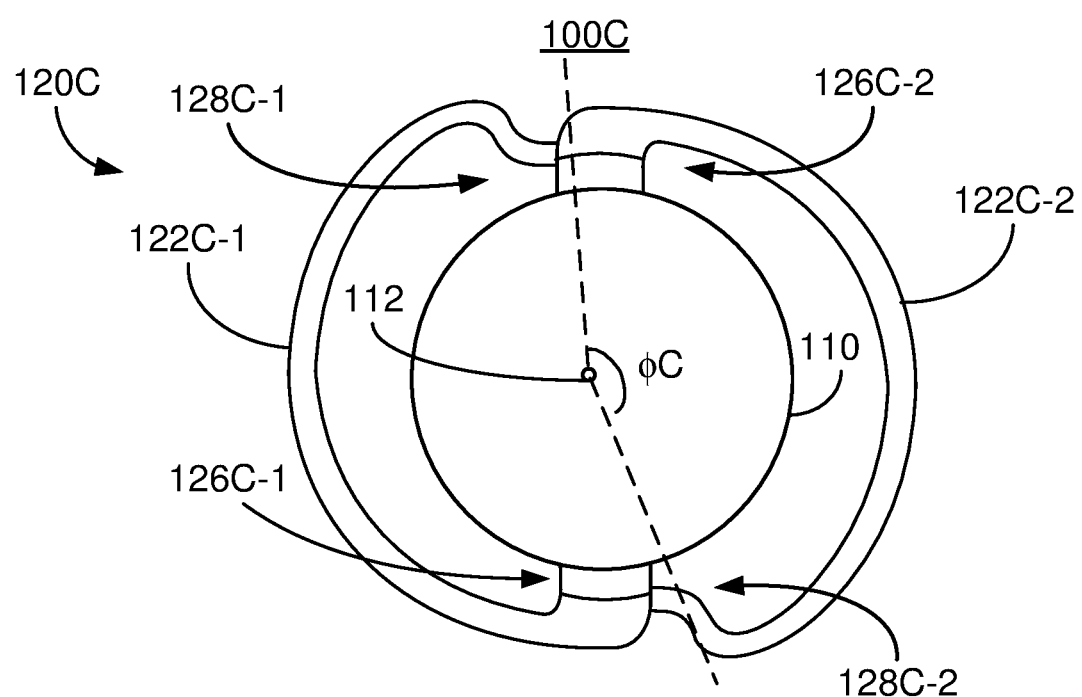
FIG. 3 depicts another exemplary embodiment of an ophthalmic device having an asymmetric hinged closed-loop haptic structure.

FIG. 3 depicts another exemplary embodiment of an ophthalmic device 100C having an optic 110 and a closed-loop haptic structure 120C. For simplicity, the ophthalmic device 100C is also referred to as an IOL 100C. The IOL 100C is analogous to the IOL 100A and/or 100B. Consequently, analogous components have similar labels. Thus, the optic 110 and closed-loop haptic structure 120C are analogous to the optic 110 and closed-loop haptic structure 120A and 120B. For clarity, FIG. 3 is not to scale and not all components may be shown.

The optic 110 may be a refractive and/or diffractive lens and may be monofocal or multifocal. The closed-loop haptic structure 120C includes closed loops 122C-1 and 122C-2 (collectively or generically 122C), hinges 126C-1 and 126C-2 (collectively or generically 126C) that are analogous to closed loops 122A-1 and 122A-2, hinges 126A-1, 126A-2, 126B-1 and 126B-2, respectively. In the embodiment shown in FIG. 3, the frame is omitted. Thus, the loops 122C are connected to the optic 110. However, in other embodiments, the frame might be included. The haptic structure 120C and optic 110 may be fabricated together or formed separately and then connected.

The closed loops 122BC retain the IOL 100C in position in the patient's eye by bearing upon the capsular bag. Each of the loops 122C subtends an angle, ϕC. In some embodiments, the magnitude of ϕC is substantially the same as that for ϕB.

The hinges 126C are configured and function in an analogous manner to the hinges 126A and 126B. Each hinge 126C has a radial section and an axial section that are connected through a bend that is substantially ninety degrees. The axial section is in the angular direction that is opposite to the second section of the first hinge because these two sections meet in the loop 122C. Each hinge 126C is stiffer in at least the radial section than the hinge 124A/124B. For example, at least the radial section of the hinge 126C has a larger cross-sectional area, has a larger thickness, has a larger width and/or is formed of a stiffer material than the relevant portions of the hinge 124A/124B. As a result, the hinge 126C is more stable than the hinges 124. Although each of the closed loops 122C is shown as including two hinges, in another embodiment, each loop 122C may have another number of hinges 124B and/or 126B. Further, although two loops 122C are shown, in another embodiment, another number of loops might be present.

In addition, the haptic structure 120C includes connecting hinges 128C-1 and 128C-2 (collectively or generically 128C). The connecting hinge 128C-1 connects the loop 120C-1 to the loop 128C-2. Similarly, the connecting hinge 128C-2 connects the loop 120C-2 to the loop 128C-1. Connecting hinges 128C are thus connecting hinges analogous to connectors 128B. Each connecting hinge 128C is an s-bend that connects one loop 122C-1 to an adjacent loop 122C-2. The connecting hinges 128C also bend when the loops 122C are compressed. The hinges 128C may improve the stability of the haptic structure 120B and help ensure that the loops 122B remain in plane when under compression. However, like the hinges 124A and 124B, the connecting hinges 128C are smaller in cross-sectional area and/or stiffness than the hinges 126C.

The IOL 100C may share some or all of the benefits of the IOL 100A and/or 100B. The large angle ϕC allows the closed-loop haptic structure 120C to contact a larger portion of the capsular bag. In some embodiments, the angle ϕC is approximately the same as ϕA and/or ϕB. In some embodiments, ϕC is approximately one hundred and eighty degrees. Thus, the loops 120C may maintain contact with the capsular bag substantially all the way around periphery of the optic 110. This may improve the stability of the IOL 100C, reduce striae in the capsular bag, and mitigate or prevent PCO. Sharp edges for the closed-loop haptic structure 120C may further reduce PCO. Hinges 126C and 128C allow the closed-loop haptic structure 120C to respond more predictably to and be more likely to remain in plane in response to a compression. Thus, performance of the IOL 100C may be improved.

Various features of the IOLs 100A, 100B and 100C have been described herein. One of ordinary skill in the art will recognize that one or more of these features may be combined in manners not explicitly disclosed herein and that are not inconsistent with the method and apparatus described.

It will be appreciated that various of the above-disclosed and other features and functions, or alternatives thereof, may be desirably combined into many other different devices or applications. It will also be appreciated that various presently unforeseen or unanticipated alternatives, modifications, variations or improvements therein may be subsequently made by those skilled in the art which alternatives, variations and improvements are also intended to be encompassed by the following claims.

The invention claimed is:

1. An intraocular lens, comprising:
an optic including an optic axis; and
a closed-loop haptic structure coupled with the optic, the closed-loop haptic structure comprising a first closed loop and a second closed loop, wherein:
the first closed loop comprises a first hinge coupling a first end of the first closed loop to the optic and a first connecting hinge, wherein the first connecting hinge comprises an s-bend coupling a second end of the first closed loop to a second hinge of the second closed loop; and the second closed loop further comprises a second connecting hinge coupling a second end of the second closed loop to the first hinge of the first closed loop, wherein:

the first hinge of the first closed loop further comprises a first radial section and a first axial section extending from the first radial section;

the second hinge of the second closed loop further comprises a second radial section and a second axial section extending from a first side of the second radial section; and the first connecting hinge is directly connected to the second radial section of the second hinge at a second side of the second radial section, wherein the first side is different from the second side, and wherein the shape of the second axial section is different from the shape of the first connecting hinge.

2. The intraocular lens of claim 1, wherein the first closed loop subtends an angle of at least 90 degrees.

3. The intraocular lens of claim 1, wherein the first closed loop subtends an angle of at least 120 degrees.

4. The intraocular lens of claim 1, wherein the closed-loop haptic structure encircles the optic over an angle of 360 degrees.

* * * * *